United States Patent [19]

Bell et al.

[11] 4,349,559
[45] Sep. 14, 1982

[54] ANTI-INFLAMMATORY SPIRO-2H-INDENE-[2,3']-3H-PYRAZOLO[4",5":7',6']NAPHTHO[2,1-B]PYRAN-1,3-DIONE DERIVATIVES

[75] Inventors: Malcolm R. Bell, East Greenbush; John L. Herrmann, Jr., Kinderhook, both of N.Y.

[73] Assignee: Sterling Drug Inc., New York, N.Y.

[21] Appl. No.: 236,216

[22] Filed: Feb. 19, 1981

[51] Int. Cl.³ .............. A61K 31/415; C07D 491/107
[52] U.S. Cl. .................................. 424/273 P; 548/369
[58] Field of Search .................... 548/369; 424/273 P

[56] References Cited

PUBLICATIONS

Fried et al., J. Am. Chem. Soc. 85, 236–238 (1963).

*Primary Examiner*—Henry R. Jiles
*Assistant Examiner*—Natalia Harkaway
*Attorney, Agent, or Firm*—Thomas L. Johnson; B. Woodrow Wyatt

[57] ABSTRACT

The compounds of formula

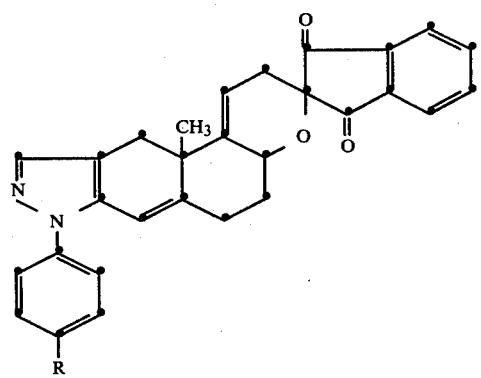

where R is hydrogen or fluorine possess glucocorticoid activity, and are prepared by reacting a compound of the formula

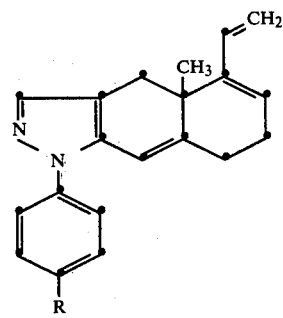

with 1,2,3-indantrione.

5 Claims, No Drawings

ANTI-INFLAMMATORY SPIRO-2H-INDENE-[2,3']-3H-PYRAZOLO[4",5":7',6']NAPHTHO[2,1-B]PYRAN-1,3-DIONE DERIVATIVES

BACKGROUND OF THE INVENTION (1) Field of the Invention

The present invention relates to novel polycyclic fused pyrazole compounds, their use as anti-inflammatory agents, and a method of preparation thereof.

(2) Description of the Prior Art

Typical glucocorticoid activity is rarely found in structures which do not possess an intact steroid nucleus. Such activity is found in naturally occurring steroids such as cortisone, hydrocortisone and aldosterone, as well as numerous synthetic modifications thereof, all containing the intact steroid nucleus. An example of a synthetic cortical steroid having high activity is a fluorophenylpyrazole derivative reported by Fried et al., J. Am. Chem. Soc. 85, 236 (1963), having the structure

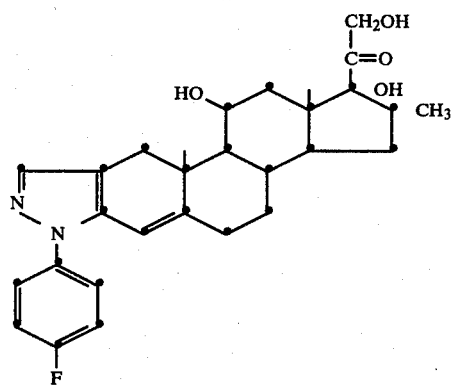

SUMMARY OF THE INVENTION

In a product aspect, the invention relates to compounds having the formula:

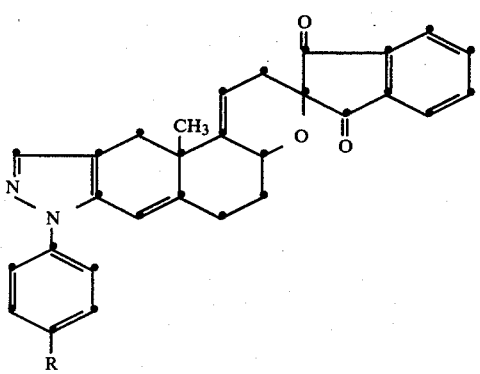

where R is hydrogen or fluorine.

In a further product aspect, the invention relates to a pharmaceutical composition for treating inflammation in mammals which comprises an anti-inflammatorily effective amount of a compound of formula I and a pharmaceutically acceptable carrier.

In a process aspect, the invention relates to a process for preparing a compound of formula I by reacting a compound of the formula:

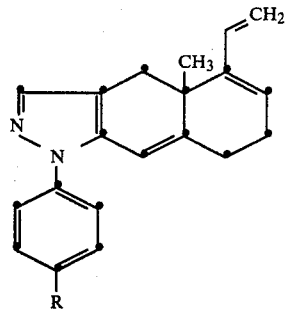

with 1,2,3-indantrione.

In a further process aspect, the invention relates to a method of reducing inflammation in a mammal which comprises administering to said mammal as anti-inflammatorily effective amount of a compound of formula I.

DETAILED DESCRIPTION INCLUSIVE OF PREFERRED EMBODIMENTS

The intermediates of formula II are prepared from a known starting material, 5-ethenyl-4,4a,7,8-tetrahydro-4a-methyl-2(3H)-naphthalenone (cf. Bell et al. U.S. Pat. No. 4,157,349, June 5, 1979) in accordance with the following reactions:

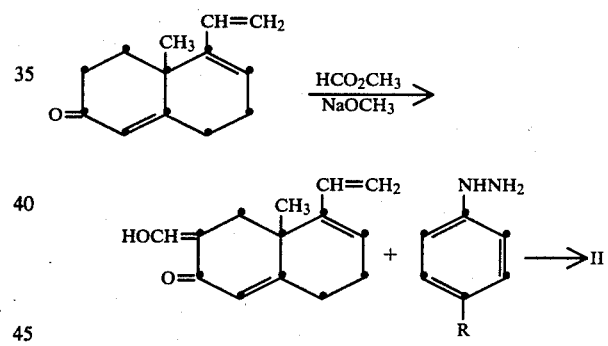

The trienone starting material is reacted with methyl formate in the presence of sodium methoxide in an inert solvent such as tetrahydrofuran to afford 5-ethenyl-3-hydroxymethylene-4,4a,7,8-tetrahydro-4a-methyl-2(3H)-naphthalenone, and the latter is then reacted with phenylhydrazine or 4-fluorophenylhydrazine or an acid-addition salt thereof in the presence of acetic acid to give the compound of formula II.

A compound of formula I is prepared by reacting a compound of formula II with 1,2,3-indantrione. The reaction takes place by heating the reactants in an inert solvent at a temperature between about 50° and 150° C.

The compounds of formula I exhibit an endocrinological profile characteristic of compounds possessing glucocorticoid properties and systemic and/or topical anti-inflammatory activity; cf. R. H. Silber, The Biology of Anti-inflammatory Steroids, Annals of the New York Academy of Sciences, Vol. 82, Art. 4, pp. 821-828.

When the compounds of formula I are administered orally to rats they cause a significant depression in thymus weight, adrenal weight and body weight gain without a change in food consumption.

The compound of formula I where R is F has also been found to possess oral glucocorticoid activity by the liver glycogen deposition test and anti-inflammatory activity by the α-tocopherol pouch test in rats.

The test procedures used to determine the biological activities of the compounds of the invention were carried out as follows:

Endocrine Profile: Mature female rats with an average body weight of 202 g and a body weight range of 15 g or less were medicated orally with test compound for 2 weeks. The test compound was prepared as a solution or suspension in 1% gum tragacanth or 0.75% methyl cellulose. On the day following the last medication, the rats were killed and the thymus and adrenal of each rat were removed, cleaned, and weighed. Body weights and food consumptions were also recorded.

Anti-inflammatory Activity (α-tocopherol pouch test): Male rats which weighed 120 g were selected for testing. A rapid subcutaneous injection of 25 mL of air was made between the scapulae of each rat. This resulted in the establishment of an airfilled pouch into which 0.5 mL of dl-α-tocopherol was injected. The test compound was administered in daily oral doses for 7 days beginning on the day of pouch formation. The compound to be tested was suspended in 1% gum tragacanth. Twenty-four hours after the last medication, the pouches were dissected free, and the fluid volume was measured. The inhibition of liquid exudate is a measure of the anti-inflammatory activity.

Glycogenic Activity: Mature male rats were bilaterally adrenalectomized 5 days prior to the test. These rats were medicated orally with the test compound for 5 days. Seven hours after the last medication, the rats (which have been fasted overnight) were anesthetized with sodium pentobarbital and a portion of one lobe of the liver was removed and frozen on dry ice for subsequent glycogen determination.

The compounds of the invention can be formulated for topical application by solution or dispersion in a conventional pharmaceutically acceptable liquid, cream or ointment base. The effective ingredient is preferably present in a concentration of 0.01% to 5.0% by weight.

The compounds of the invention can be formulated for oral administration in tablet or capsule form with conventional excipients. The active ingredient is preferably present in an amount of 1 mg to 100 mg per unit dosage form.

The following examples will further illustrate the invention.

EXAMPLE 1

(a)

5-Ethenyl-3-hydroxymethylene-4,4a,7,8-tetrahydro-4a-methyl-2(3H)-naphthalenone.

A solution of 50.0 g (0.265 mol) of 5-ethenyl-4,4a,7,8-tetrahydro-4a-methyl-2(3H)-naphthalenone in 350 mL of tetrahydrofuran was cooled to −5° C. in an ice-methanol bath and stirred under nitrogen while 57.2 g (1.06 mol) of sodium methoxide was added. The resulting mixture was stirred for 30 min at −5° C. and then a solution of 114 mL (1.86 mol) of methyl formate in 100 mL of tetrahydrofuran was added slowly. The mixture was stirred overnight at room temperature and then poured onto a mixture of ice-water (1500 mL) and 6 N hydrochloric acid (265 mL). The product was extracted with ether and the combined extracts were washed with water. The dried extract was dried over anhydrous magnesium sulfate and concentrated in vacuo to afford an oil. This oil was triturated with hexane (4×250 mL) and the combined triturates were dried over magnesium sulfate and concentrated in vacuo to afford 55.37 g of a red oil, consisting essentially of the above-entitled compound as established by proton NMR (PMR) spectral data.

(b)

1-Ethenyl-6-(4-fluorophenyl)-3,4,9,9a-tetrahydro-9a-methyl-6H-naphtho[2,3-c]pyrazole (II; R=F).

4-Fluorophenylhydrazine hydrochloride (45.85 g, 0.282 mol) and sodium acetate (23.14 g, 0.282 mol) were added to a solution of 55.37 g (0.256 mol) of the product obtained in part (a) above in 225 mL of glacial acetic acid. The mixture was stirred overnight at room temperature and then concentrated in vacuo to afford a semi-solid. This material was suspended in ether (1 L) and filtered to remove sodium chloride. The ether filtrate was washed with water (4×250 mL), saturated sodium bicarbonate (until weakly basic) and saturated sodium chloride (100 mL). The extract was dried over anhydrous magnesium sulfate, decolorized with charcoal and concentrated in vacuo to afford an oil. This oil was triturated with 1:2 ether-hexane (3×750 mL) to afford 69.58 g of a dark brown oil. An analytical sample was prepared by using high-performance liquid chromatography with 1:3 ether-hexane as solvent. The resulting yellow oil was triturated with pentane to afford 1-ethenyl-6-(4-fluorophenyl)-3,4,9,9a-tetrahydro-9a-methyl-6H-naphtho[2,3-c]-pyrazole (II; R=F) as a yellow solid, m.p. 70°–72° C., with a consistent PMR spectrum.

(c)

8'-(4-Fluorophenyl)-2',3',5',6',11',11a'-hexahydro-11a'-methylspiro-2H-indene[2,3']-3H-pyrazolo[4'',5'':7',6']-naphtho[2,1-b]pyran-1,3-dione (I; R=F).

A mixture of 15.3 g (0.05 mol) of II (R=F) (part b above) and 9.8 g (0.055 mol) of 1,2,3-indantrione monohydrate in 150 mL of xylene was refluxed for 2 hours. The cooled reaction mixture was filtered through silica gel and concentrated in vacuo. The residue was crystalized from ethanol to afford 7.19 g of I (R=F) as a tan solid, m.p. 210°–211° C. The proton NMR spectrum (PMR) was consistent with the assigned structure.

In the endocrine profile determination, Compound I (R=F) at a dose level of 1 mg/kg caused a 61% reduction in thymus weight, 56% reduction in adrenal weight and 129% reduction in body weight gain as compared with the controls. In the α-tocopherol pouch test, Compound I (R=F) was active with $ED_{50}$=10 mg/kg. In the glycogenic activity test, Compound I (R=F) at a dose level of 9 mg/kg/day×5 produced a liver glycogen deposition value of 21.8±4.4 mg/g of tissue as compared to 2.2±0.04 mg/g for the vehicle (1% gum tragacanth) alone.

EXAMPLE 2

(a) 1-Ethenyl-6-phenyl-3,4,9,9a-tetrahydro-9a-methyl-6H-naphtho[2,3-c]pyrazole (II; R=H) was prepared according to the procedure of Example 1, part (b), while substituting a molar equivalent amount of phenylhydrazine hydrochloride for the 4-fluorophenylhydrazine hydrochloride of that example. The product was characterized by its PMR spectrum.

2',3',5',6',11'11a'-Hexahydro-11a'-methyl-8'-phenyl-spiro-2H-indene[2,3']-3H-pyrazolo[4",5":7',6']naphtho[2,1-b]pyran-1,3-dione (I; R=H).

A mixture of 14.42 g (0.05 mol) of II (R=H) (part a above) and 9.88 g (0.06 mol) of 1,2,3-indantrione monohydrate in 150 mL xylene was refluxed for 2 hours, then allowed to stand at room temperature for 55 hours and filtered to afford a green solid. This green solid was dissolved in methylene dichloride, filtered through silica gel and the solvent removed in vacuo. The residue was triturated with ether to afford 10.95 g of I (R=H) as a yellow solid, m.p. 209°–210° C. The PMR spectrum was consistent with the assigned structure.

In the endocrine profile determination, Compound I (R=H) at a dose level of 5 mg/kg caused a 51% reduction in thymus weight, 38% reduction in adrenal weight, and 62% reduction in body weight gain as compared with the controls. Compound I (R=H) was inactive in the α-tocopherol pouch test at a dose level of 100 mg/kg.

We claim:

1. A compound of the formula

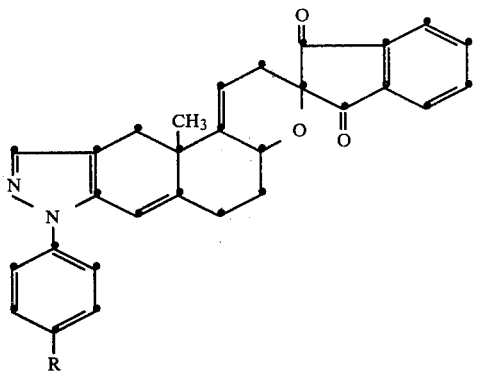

where R is hydrogen or fluorine.

2. 8'-(4-Fluorophenyl)-2',3',5',6',11',11a'-hexahydro-11a'-methylspiro-2H-indene[2,3']-3H-pyrazolo[4",5":7',6']-naphtho[2,1-b]pyran-1,3-dione, according to claim 1.

3. [4',5',6',8",11',11a'-Hexahydro-11a',-methyl-8-]2',3',5',6',11',11a'-Hexahydro-11a'-methyl-8'-phenyl-spiro-2H-indene[2,3']-3H-pyrazolo[4",5":7',6']-naphtho[2,1-b]pyran-1,3-dione, according to claim 1.

4. A pharmaceutical composition for treating inflammation in mammals which comprises an anti-inflammatorily effective amount of a compound according to claim 1 and a pharmaceutically acceptable carrier.

5. A method of reducing inflammation in a mammal which comprises administering to said mammal an anti-inflammatorily effective amount of a compound according to claim 1.

* * * * *

UNITED STATES PATENT AND TRADEMARK OFFICE
CERTIFICATE OF CORRECTION

PATENT NO. : 4,349,559
DATED : September 14, 1982
INVENTOR(S) : Malcolm R. Bell and John L. Herrmann, Jr.

It is certified that error appears in the above—identified patent and that said Letters Patent are hereby corrected as shown below:

Column 2, line 21, "as" should read --an--.

Column 3, line 61, "1.86 mol" should read --1.85 mol--.

Column 6, line 22, Claim 3, delete "[4',5',6',8",11',11a'-Hexahydro-11a',-methyl-8-]".

Column 6, line 24, Claim 3, "[4",5':7',6']" should read --[4",5":7',6']--.

Signed and Sealed this

First Day of February 1983

[SEAL]

Attest:

Attesting Officer

GERALD J. MOSSINGHOFF
Commissioner of Patents and Trademarks